United States Patent [19]
Petzold et al.

[11] Patent Number: 5,495,751
[45] Date of Patent: Mar. 5, 1996

[54] STREAMING POTENTIAL MEASURING CELL

[75] Inventors: James C. Petzold, Reading; Roger A. Allen, Prestwood, both of Great Britain

[73] Assignee: The Wiggins Teape Group Limited, Basingstoke, England

[21] Appl. No.: 146,118

[22] PCT Filed: May 12, 1992

[86] PCT No.: PCT/GB92/00852

§ 371 Date: Nov. 12, 1993

§ 102(e) Date: Nov. 12, 1993

[87] PCT Pub. No.: WO92/21026

PCT Pub. Date: Nov. 26, 1992

[30] Foreign Application Priority Data

May 13, 1991 [GB] United Kingdom ............ 9110318

[51] Int. Cl.⁶ .................................. G01N 27/00
[52] U.S. Cl. .............. 73/53.03; 73/53.04; 324/71.1
[58] Field of Search .................. 73/53.03; 324/71.1

[56] References Cited

U.S. PATENT DOCUMENTS

| | | | |
|---|---|---|---|
| 2,602,325 | 7/1952 | Campbell et al. | 73/53.03 |
| 4,535,285 | 8/1985 | Evans et al. | 324/71.1 |
| 4,687,986 | 8/1987 | Eriksson | 324/71.1 |
| 5,069,753 | 12/1991 | Nishi | 73/53.03 X |

FOREIGN PATENT DOCUMENTS

WO86/00707  1/1986  WIPO ................. 324/71.1

Primary Examiner—Hezron E. Williams
Assistant Examiner—J. David Wiggins
Attorney, Agent, or Firm—Burns, Doane, Swecker & Mathis

[57] ABSTRACT

A cell for measuring electrokinetic potential, such as a streaming potential, includes a housing having an interior chamber divided into an upper compartment and a lower compartment by a filter mesh on which is formed a pad of a fibrous dispersion to be measured. The cell is of particular utility in the manufacture of paper and is used in the manner described in U.S. Pat. No. 4,535,285. To assist flushing of the fiber pad from the filter mesh a nozzle assembly in the upper compartment is used to direct a jet of water at the filter mesh. An additional step to flush out fibrous material reaching the upper compartment is described. This uses an additional port.

11 Claims, 1 Drawing Sheet

STREAMING POTENTIAL MEASURING CELL

FIELD OF THE INVENTION

This invention relates to a measurement cell for use in measuring an electrokinetic potential of a fibrous dispersion and to a measurement system using such a cell.

The furnish or stock supplied to a paper-making machine has certain electrical characteristics associated with it which affect the formation of the paper web on the Foudrinier wire. In particular there is a potential known as Zeta potential which is more usually monitored by measurement of a related potential known as streaming potential. Quality control in paper making has increased the demand for reliable, on-line measurement of streaming potential.

Streaming potential is measured by means of a cell containing a chamber divided into two compartments by a filter mesh. A sample of the furnish is introduced into one compartment, the other being open, and a pad of fibrous material is formed on one side of the mesh. A controlled pressure differential is applied to the fluid in the compartments and appears across the measurement pad. This results in the development of streaming potential which is measured by two electrodes in the cell located on opposite sides of the pad.

BACKGROUND OF THE INVENTION

Embodiments of cells for measuring streaming potential are described in European patent EP-B-0 079 726. The patent also describes a preferred measurement system in which the cell is to be connected and a measurement cycle for reliably obtaining streaming potentials. The cell has been found to provide a good, reliable on-line performance. However, certain problems can arise with prolonged on-line operation.

The cell construction disclosed in the above patent comprises two frusto-conical compartments with their wider ends adjacent but separated by the mesh on which the pad is formed from the fibres in the furnish. The narrower ends of the cones provide inlet and outlet ports respectively. The cell assembly is mounted vertically with the mesh horizontal. The pad is formed on the underside of the mesh by introducing furnish to the lower compartment. After measurement the pad is back-flushed from the mesh by fresh water admitted through the upper compartment port. To aid flushing an apertured cone is located in the upper compartment with the intention of distributing flushing water over the whole pad area. The pad is very firmly compacted on the mesh and it has been found that it is not always easy to remove it entirely.

A second problem is that in forming the pad, fines, that is finer fibres and particles in the furnish, flow through the mesh into the upper compartment. Their presence in the upper compartment may affect the potential measured. Over a number of measurement cycles, these fines may accumulate on the upper side of the mesh with increasing effect and may also obstruct the back flushing procedure.

The present invention enables us to provide a means for better ensuring that the pad material is flushed from the mesh before the next measurement cycle commences and evacuating fines from the upper compartment in each measurement cycle.

SUMMARY OF THE INVENTION

According one aspect of the present invention there is provided a measurement cell for measuring an electrokinetic potential of a fibrous dispersion comprising a housing having an internal chamber divided into two compartments by a filter mesh, a port in one compartment for introducing a fibrous dispersion into the chamber to form a fibrous pad on one side of the filter mesh, and means for introducing a fluid into the other compartment to flush the pad from the filter mesh, characterised in that:

said fluid-introducing means comprises a nozzle adapted to provide a cone of pressurized-fluid spray over the side of the filter mesh facing said other compartments.

Preferably the above-mentioned nozzle is adapted to provide the cone of pressurized spray with the axis of the cone aligned with the central axis of the filter mesh.

The other compartment of the cell may further comprise a port allowing fluid from the nozzle to be circulated through the other compartment to flush out material from the fibrous dispersion that enters the other compartment.

According to another aspect of the invention there is provided a measurement system for measuring an electrokinetic potential of a fibrous dispersion employing a measurement cell of the kind in which a chamber is divided into two compartments by a filter mesh and comprising a control arrangement which establishes a measurement sequence in which a measurement pad is formed on one side of the filter mesh by introducing a fibrous dispersion into one compartment, a potential measurement is made with the measurement pad, and the pad is subsequently flushed from the cell, characterised in that:

the other compartment has a fluid inlet and has a fluid outlet in a wall thereof; and the control arrangement is operable to simultaneously open said fluid inlet and fluid outlet to allow a flushing fluid to be passed through the other compartment to remove therefrom material from the fibrous dispersion that may have entered into the other compartment.

In the operation of the above measurement system the flushing of said material from the other compartment may be performed after making a potential measurement with the measurement pad but before the pad is flushed from the cell.

BRIEF DESCRIPTION OF THE DRAWINGS

The invention and its preferred practice will be further described with reference to the embodiment illustrated in the accompanying drawings in which.

THE PREFERRED EMBODIMENT

Figure 1:
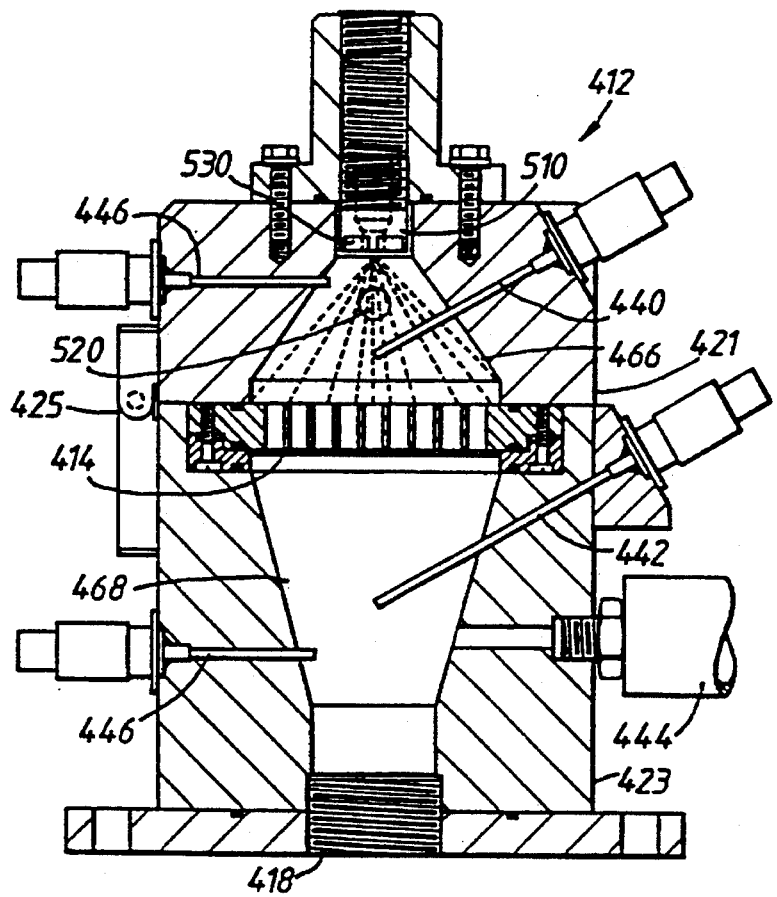
FIG. 1 shows a longitudinal axial section through the measurement cell.

The general construction of the measuring cell embodying the present invention follows that disclosed in EP-B 0 079 726. The cell is intended for connection in a circuit such as shown in FIG. 1 of the prior patent for making measurement cycles as described. However, to obtain the benefits of the cell improvements to be described, the circuit is also modified as will be described with reference to FIG. 2. The following description will, therefore, be particularly directed to the modifications of the cell by which the present invention is implemented.

The cell 412 comprises a two-part housing defining an internal chamber divided into two compartments: an upper inverted, shallow, frusto-conical compartment 466 whose wider end adjoins the wider end of a second frusto-conical compartment 468 of steeper taper. The lower end of compartment 468 contains a port 418 for the selective introduction of samples of the furnish being measured and the flushing to drain of the pad after measurement. The compartments 466 and 468 are separated by a removable filter mesh 414.

The housing 412 is in two parts, an upper part 421 defining the upper compartment 466 and a lower part 423 which defines the lower compartment 468 and in the top of which seats a removable filter assembly supporting the filter mesh 414 on the lower side thereof. The filter assembly is of a construction generally similar to that described in EP-B 0 079 726. The two housing parts 421, 423 are pivotally mounted by hinge 425 to allow the cell to be opened for access to the interior of the cell and removal of the filter assembly. In normal operation the housing parts are maintained in the closed position illustrated by bolts (not shown).

The compartments 466 and 468 have respective streaming potential measuring electrodes 440 and 442, formed of silver/silver oxide, projecting into them. The cell also includes a pressure measurement unit 444. Electrodes 446 are also incorporated in the cell to facilitate regeneration of the silver electrodes when required. The use of silver/silver oxide electrodes and the regenerative technique used for them is described in our copending International application PCT/GB91/0173 published under the number WO 92/06368. The cell is intended for use in a measurement cycle as previously described in detail in EP-B 0 079 726. However, the present measurement cell contains provision to better flush the pad from the cell and to ensure fines from the furnish do not accumulate on the upper surface of the filter mesh.

To this end the upper compartment 466 is provided with two ports 510 and 520 allowing fluid entry and egress respectively from compartment 466. The first port 510 is located at the cone apex and is closed by a water jet assembly 530. To allow fluid egress from the upper chamber, the second port 520 is provided offset in the compartment wall.

Figure 2:
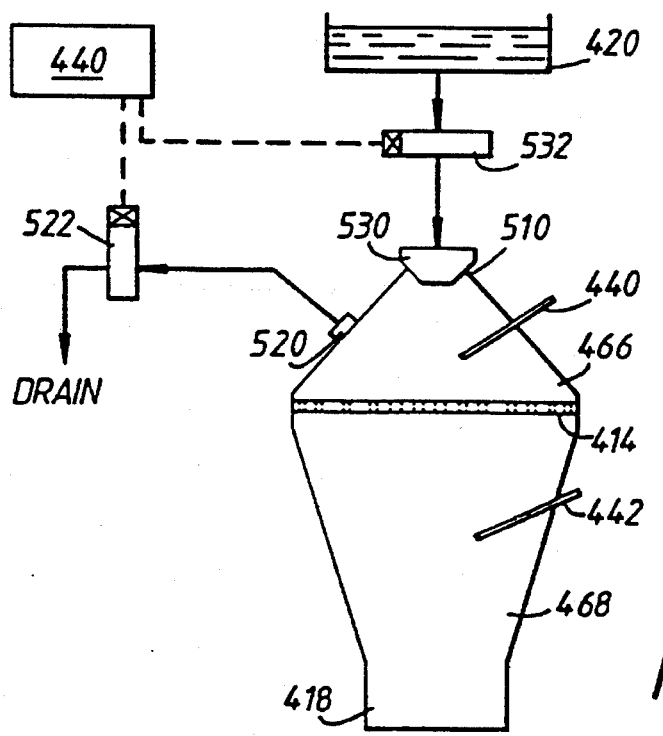
FIG. 2 shows the cell diagrammatically in circuit with other components used in the control of its operation.

The operation of the measuring cell follows the pad build—pad hold/measure—pad flush routine described in the EP-B 0 079 726 with some modification and an addition. FIG. 2 illustrates circuit changes associated with the upper compartment ports which enable the modified and additional functions to be performed. During pad build, the port 418 is connected to receive the furnish sample to be measured. The port 520 is open to drain to allow the furnish water to rise through the filter mesh. Having formed the measurement pad on the underside of the mesh, the streaming potential measurement is made as previously disclosed, with port 520 remaining open to drain to establish the low (zero) reference pressure in the upper compartment.

After the measurement sequence an additional preliminary flushing step is performed in the upper compartment. The water jet assembly 530 is turned on at the normal pressure from the public water supply 420 to flush out through port 520 any fines from the upper compartment that could disturb the measurement or accumulate on the upper surface of the mesh during the course of repeated measurement cycles. After this preliminary flushing phase port 520 is closed, and the pad back flushed out of the lower chamber port 418 by use of the water jet assembly 530. The water jet assembly is designed and mounted to provide a full cone of flushing fluid over the whole upper surface of the filter mesh.

Suitable jet assemblies are described in U.S. Pat. Nos. 3,104,829 and 3,146,674 and are sold under the name "Fulljet Nozzles" by Spraying Systems Co. of Bellwood, Ill., U.S.A. A "Fulljet Nozzle" No. ½HH40 has been satisfactorily employed providing a spray cone angle of 45° at mains water supply pressure in the pad removal phase.

The selective opening and closing outlet port 520 is done through solenoid-controlled valve 522. The supply of water from source 420 to jet nozzle assembly 530 is controlled by electrically-actuable valve 532 settable between closed and fully open positions. The valves 522 and 532 are under the control of computer 540 which also controls the operation of the remainder of the measurement system.

It will be understood that flushing of the upper compartment may be performed at times other than that described.

We claim:

1. A measurement cell for measuring an electrokinetic potential of a fibrous dispersion comprising a housing having an internal chamber divided into two compartments by a filter mesh, a port in one compartment for introducing a fibrous dispersion into the chamber to form a fibrous pad on one side of the filter mesh, and means for introducing a fluid into the other compartment to flush the pad from the filter mesh, wherein:

said fluid-introducing means comprises a nozzle adapted to provide a full cone of pressurized-fluid spray over the side of the filter mesh facing said other compartment.

2. A measurement cell as claimed in claim 1 in which said nozzle is mounted to provide said cone of pressurized spray with the axis of the cone aligned with the central axis of the filter mesh.

3. A measurement cell as claimed in claim 1 or 2 in which said other compartment includes a port allowing fluid from said nozzle to be circulated through said other compartment to flush out material from the fibrous dispersion that enters said other compartment.

4. A measurement system for measuring an electrokinetic potential of a fibrous dispersion employing a measurement cell of the kind in which a chamber is divided into two compartments by a filter mesh and comprising a control arrangement which establishes a measurement sequence in which a measurement pad is formed on one side of the filter mesh by introducing a fibrous dispersion into one compartment, a potential measurement is made with the measurement pad, and the pad is subsequently flushed from the cell, wherein:

the other compartment has a fluid inlet and has a fluid outlet in a wall thereof; the control arrangement is operable to simultaneously open said fluid inlet and said fluid outlet to allow a flushing fluid to be passed through the other compartment to remove therefrom material from the fibrous dispersion that may have entered into the other compartment; and said inlet comprises a nozzle for providing a pressurised-fluid spray over the side of the filter mesh facing said other compartment.

5. A measurement system as claimed in claim 4 in which the flushing of said material from the other compartment is performed after making a potential measurement with the measurement pad but before the pad is flushed from the cell.

6. A measurement system as claimed in claim 4 or 5 in which said control arrangement comprises a first and a second valve connected to said inlet and to said outlet respectively and said measurement sequence includes a step in which said first and second valves are simultaneously opened to allow flushing of said material from the other compartment.

7. A measurement system as claimed in claim 5 in which the measurement sequence includes another step at which said first valve is opened and said second valve is closed to allow flushing of the measurement pad from the filter mesh.

8. A measurement system for measuring an electrokinetic potential of a fibrous dispersion comprising:

a housing having an internal chamber divided into first and second compartments;

filter mesh with a first side between the first and second compartments;

the first compartment including a port for introduction of a fibrous dispersion thereinto to form a fibrous pad on the first side of the filter mesh;

the second compartment has a wall with a fluid inlet and a fluid outlet;

means for introducing a fluid into the second compartment to flush the fibrous pad from the filter mesh;

potential measurement means for measuring the potential of the fibrous pad;

control means for establishing a measurement sequence including the steps of forming a measurement pad on the first side of the mesh by the means for introducing a fibrous dispersion, measuring the potential of the measurement pad with the potential measurement means, and flushing the measurement pad from the chambers, and being operable to simultaneously open the fluid inlet and the fluid outlet to allow a flushing fluid to pass through the second compartment to remove material from the fibrous dispersion that may have entered the second compartment; and wherein the inlet opening includes a nozzle directed along the second side of the filter mesh facing the second compartment so that a pressurized-fluid spray can be provided.

9. The measurement system of claim 8 wherein the control means flushes material of the fibrous dispersion from the second compartment after measuring the potential of the measurement pad, and before the means for introducing fluid is actuated.

10. The measurement system of claim 8 or claim 9 wherein the control means includes a first valve connected to the inlet and a second valve connected to the outlet, and operates to simultaneously open the first and second valves to allow flushing of material from the second compartment.

11. The measurement system of claim 10 wherein the control means is operable to open the first valve while the second valve is closed to allow flushing of the measurement pad from the filter mesh.

* * * * *